United States Patent
Idelevich et al.

(10) Patent No.: US 12,065,687 B2
(45) Date of Patent: Aug. 20, 2024

(54) DEVICE AND METHOD FOR TREATING FLUIDS, PARTICULARLY BODY FLUIDS

(71) Applicant: Bruker Daltonik GmbH, Bremen (DE)

(72) Inventors: Evgeny Idelevich, Münster (DE); Karsten Becker, Laer (DE)

( * ) Notice: Subject to any disclaimer, the term of this patent is extended or adjusted under 35 U.S.C. 154(b) by 869 days.

(21) Appl. No.: 15/747,643

(22) PCT Filed: Jul. 28, 2016

(86) PCT No.: PCT/EP2016/068039
§ 371 (c)(1),
(2) Date: May 4, 2018

(87) PCT Pub. No.: WO2017/017206
PCT Pub. Date: Feb. 2, 2017

(65) Prior Publication Data
US 2018/0230508 A1    Aug. 16, 2018

(30) Foreign Application Priority Data

Jul. 29, 2015    (DE) .................. 10 2015 112 343.6

(51) Int. Cl.
*C12Q 1/04* (2006.01)
*B01L 3/00* (2006.01)
(Continued)

(52) U.S. Cl.
CPC ................ *C12Q 1/04* (2013.01); *B01L 3/502* (2013.01); *C12M 33/04* (2013.01); *C12M 47/04* (2013.01); *C12Q 1/24* (2013.01); *G01N 1/4077* (2013.01); *B01L 2200/141* (2013.01); *B01L 2300/0681* (2013.01); *B01L 2400/0478* (2013.01);
(Continued)

(58) Field of Classification Search
CPC .. C12Q 1/04; C12Q 1/24; B01L 3/502; B01L 2300/0681; B01L 2400/0478; B01L 2400/0605; G01N 1/4077; G01N 2001/4088; G01N 33/491; C12M 47/02;
(Continued)

(56) References Cited

U.S. PATENT DOCUMENTS 2,923,669 A * 2/1960 Poitras .................. C12M 23/10
435/297.5
3,931,010 A    1/1976 Ayres et al.
(Continued)

FOREIGN PATENT DOCUMENTS

CN    102753675 A    10/2012
DE    9304954 U1    8/1993
(Continued)

*Primary Examiner* — Jill A Warden
*Assistant Examiner* — Henry H Nguyen
(74) *Attorney, Agent, or Firm* — Benoît & Côté Inc.

(57) ABSTRACT

A device for treating fluids, particularly body fluids, comprises a receiving container for receiving the fluid from a body, a filter device which comprises a filter element for filtering out pathogenic particles from the fluid, and a cultivation device configured to incubate the filtered pathogenic particles on a nutrient medium, the filter device being coupled to the cultivation device such that the pathogenic particles can be transferred from the filter element into the cultivation device without contamination. A corresponding method is also provided.

15 Claims, 4 Drawing Sheets

(51) Int. Cl.
*C12M 1/00* (2006.01)
*C12M 1/12* (2006.01)
*C12M 1/26* (2006.01)
*C12Q 1/24* (2006.01)
*G01N 1/40* (2006.01)
*G01N 33/49* (2006.01)

(52) U.S. Cl.
CPC ...... *B01L 2400/0605* (2013.01); *C12M 25/02* (2013.01); *C12M 33/14* (2013.01); *C12M 47/02* (2013.01); *G01N 2001/4088* (2013.01); *G01N 33/491* (2013.01)

(58) Field of Classification Search
CPC ...... C12M 33/04; C12M 47/04; C12M 25/02; C12M 33/14
See application file for complete search history.

(56) References Cited

U.S. PATENT DOCUMENTS

| | | | |
|---|---|---|---|
| 4,957,637 A | 9/1990 | Cornell | |
| 5,038,793 A * | 8/1991 | Guirguis | B01L 3/502 600/573 |
| 5,677,140 A | 10/1997 | Denzler | |
| 5,694,478 A * | 12/1997 | Braier | C12M 41/36 435/808 |
| 6,106,483 A * | 8/2000 | Guirguis | A61B 10/0045 600/562 |
| 6,287,849 B1 * | 9/2001 | McNerney | C12M 45/03 435/287.7 |
| 9,308,477 B2 | 4/2016 | Treharne et al. | |
| 9,409,165 B2 | 8/2016 | Ellis et al. | |
| 9,732,371 B2 | 8/2017 | Waiche et al. | |
| 9,808,798 B2 * | 11/2017 | Ismagilov | B01L 3/502738 |
| 2007/0238139 A1 * | 10/2007 | Gazenko | C12Q 1/04 435/7.32 |
| 2007/0243532 A1 | 10/2007 | Wolf et al. | |
| 2009/0269841 A1 * | 10/2009 | Wojciechowski | F04B 43/0072 435/303.1 |
| 2011/0100921 A1 * | 5/2011 | Heinrich | A61M 1/3633 210/670 |
| 2011/0124106 A1 * | 5/2011 | Froman | B01L 3/5021 435/379 |
| 2014/0017779 A1 | 1/2014 | Waiche et al. | |
| 2015/0072346 A1 * | 3/2015 | Gellibolian | B01L 3/5021 435/6.11 |

FOREIGN PATENT DOCUMENTS

| | | |
|---|---|---|
| EP | 0122581 A2 | 10/1984 |
| JP | S59196084 A | 11/1984 |
| JP | 2006071478 A | 3/2006 |
| JP | 2009118780 A | 6/2009 |
| JP | 2011515149 A | 5/2011 |
| JP | 2014524020 A | 9/2014 |
| WO | 2005087944 A1 | 9/2005 |
| WO | 2009117212 A1 | 9/2009 |
| WO | 2013/000897 A1 | 1/2013 |
| WO | 2013016211 A1 | 1/2013 |

* cited by examiner

DEVICE AND METHOD FOR TREATING FLUIDS, PARTICULARLY BODY FLUIDS

The present invention relates to a device for treating fluids, particularly body fluids (e.g. blood or liquor). The treatment of fluids according to the invention can for example be the isolation and cultivation of microorganisms from blood as body fluid. The device according to various exemplary embodiments can simultaneously serve to collect the body fluid, for example blood. In a general manner, the device described here can, in accordance with various exemplary embodiments, comprise a device for isolation of microorganisms from the fluid and a device for cultivation of the microorganisms.

Bloodstream infections (e.g. sepsis and endocarditis) are counted among the diseases with the highest mortality. An identification and sensitivity testing of the microorganism causing such an infection is crucial for a targeted, i.e. pathogen-targeted, antimicrobial treatment. A swift microbiological diagnosis is thus crucial for appropriate treatment and improves the success of the treatment.

Unfortunately the current methods based on a cultivation require 48 to 72 hours or even longer to obtain the result of the identification and sensitivity testing (also referred to as resistance determination) of the pathogen. This is because on the one hand the transportation times between the collection of the blood samples from patients and the arrival in the laboratory are often long and on the other hand, after arrival of the blood samples in the laboratory, they are monitored in accordance with current standards with respect to growth in a liquid medium in an automated blood culture system by means of continuous measurement of gas concentration changes. Only once growth has been detected in the blood sample by means of exceeding a predetermined positive gas concentration change rate and a corresponding signal triggering are the blood samples plated and incubated on a solid nutrient medium by the laboratory staff. Once the pathogen colonies have formed on the solid medium, they can be used for a precise identification and sensitivity testing. It is standard for the above-mentioned 48 to 72 hours to elapse before this stage is reached. The fact that, approximately six hours after the infection has been contracted the survival prospects for an affected person without adequate antibiotic treatment drops to 40%, illustrates the dangerous nature of a bloodstream infection, even in highly developed countries. According to recent statistics, in Germany alone more than 60,000 people die each year from so-called blood poisoning (the popular term for sepsis). The worldwide figure is estimated to be eight million deaths.

Because the microbiological results in the early and also the patient survival-determining phase of a bloodstream infection are not available, it is not possible at this stage to initiate an antimicrobial treatment which is targeted, i.e. adapted to the actual pathogen. For this reason an untargeted (calculated) broad antibiotic treatment is usually realized in order to include the likeliest pathogens in the treatment. This is achieved by the administration of so-called broad-spectrum antibiotics and/or by the combination of various antibiotics with different activity profiles. This results in increased selection pressure with respect to the formation and spread of (multi-) resistant isolates, i.e. it becomes a matter of selection of pathogens, which are characterized by their (multi-) resistance to the antibiotics used. If the blood stream infection is caused by resistance phenotypes with a very broad resistance spectrum, it is even possible for the antibiotic treatment to fail, usually with fatal consequences for the patient.

The objective of the present invention is to solve the above-mentioned problems and to provide a device which in particular simplifies the handling of body fluids obtained for diagnostic purposes and reduces the time period from collection of the body fluid up until identification of pathogens which may be present therein. Moreover, said device ensures that infections are treated faster and in a more specific manner, i.e. in a more targeted manner with substances which can be used to combat the pathogen. By this means, the patient receives an antibiotic treatment which, according to laboratory testing, is effective against the pathogen causing the infection, and the attending physician can select from the antibiotics tested and found to be effective the substance (s) which has the greatest activity for the type of infection present, which best reaches the site of action in the patient, which is the most tolerable for the patient and which has the lowest selection pressure. In the long term, this can have a positive influence on the development and spread of (multi-) resistant pathogens.

The present device for treating body fluids according to various exemplary embodiments pursues the objective of significantly reducing the time before identification and sensitivity testing by means of direct isolation of microorganisms from body fluids from a patient when a bloodstream infection is suspected or who, due to infection, may be expected to have microorganisms present in the body fluid and also by means of an immediately subsequent incubation of these microorganisms on a solid nutrient medium. This objective is achieved, amongst other things, in that the above-mentioned times for the sample intermediate storage and the sample transportation are used for the propagation of the microorganisms. In particular, the device described here is able to dispense with the time-consuming incubation of the samples in a fluid medium blood culture machine, so that also the required additional time until the positive result is obtained from the blood culture machine on the basis of the evidence of growth of the microorganisms can be saved and thus the time period from the collection of the body fluid until the identification of the infectious agents can be reduced dramatically.

In various exemplary embodiments, a device for treating fluids, particularly body fluids, is provided, which has a receptacle for receiving the fluid, in particular for receiving a body fluid derived from a (human or animal) body; a filter device, which has a filter element for filtering pathogenic particles or other components out of the fluid (e.g. certain cell fractions such as stem cells from the body fluid); and which has a cultivation device, which is designed such that the filtered out pathogenic particles are incubated on a nutrient medium, for example directly thereon. The filter device can be coupled to the cultivation device in such a way that the pathogenic particles can be transferred in a contamination-free manner from the filter element into the cultivation device. The filter element can be a filter which has a suitably selected pore size, for example in the range from approximately 100 nm to approximately 10 µm, more preferably for example in a range from approximately 200 nm to approximately 1 µm. In the context of this application, pathogenic particles can be understood to mean microorganisms of any kind including bacteria, fungi, parasites, algae and viruses and their components as well as other corpuscular components (e.g. host cells), in particular with reference to body fluids. Depending on the target filtrate, the filter membrane can be equipped/coated with antibodies or other binding molecules, such as e.g. bacteriophage components, which are adapted to the particles to be filtered out. In one exemplary embodiment, the receptacle can be a collection device, for example a syringe, by means of which for example the body fluid can also be taken in a direct manner from the (human or animal) patient. In another exemplary embodiment, the fluid can also be taken with a device (e.g. syringe) specially designed for the task and can be transferred to the receptacle for treatment.

In the context of this invention, the fluid can also be a body fluid, which has been obtained by corresponding preprocessing from non-fluid body materials. Preprocessing can mean a liquefaction, for example the production of a solution or suspension based on the non-fluid body material. Typical examples include the use of tissue and organ samples of all kinds which have been treated by chopping and/or liquefaction or of test materials obtained by means of a swab transferred to a fluid. As a further example, tissue samples from any body region (e.g. brain biopsies) are mentioned here, which can be transferred into a suspension by means of reduction (e.g. crushing) and liquefaction in the context of the preprocessing.

The present invention can however also be used with respect to any initially non-fluid materials in a liquefied form (suspension or solution), which are to be examined with respect to their components, for example swabs (material obtained by means of swabs) from any surface or deep body regions (e.g. external or internal patient surfaces) but also from surfaces outside of the body (e.g. any surrounding surfaces). The device according to the invention thus makes it possible to also treat fluids which come from material not derived from the body. It is thus possible for example with the device described here to examine water for contamination with pathogenic particles. The present invention can thus also be used for the treatment of fluids which have materials not derived from a human or animal body. In this regard, all of the features mentioned here with reference to body fluids could be transferred to other fluids not related to animal or human bodies. The receptacle of the device according to the invention can thus be used to receive any fluid to be examined, which does not necessarily have to correspond to a body fluid or a fluid having material derived from a body. The fluid present in the receptacle can then be filtered in the same way as for example a body fluid by means of the filter device, which comprises a filter element for filtering out pathogenic particles or other components. Similarly, the filtrate, in other words, the at least condensed or filtered out pathogenic particles, can subsequently be incubated on the nutrient medium. Although the use of the device according to the invention for treating a body fluid thus constitutes a preferred application and the detailed description of the device according to the invention based on the attached figures refers to this preferred case, the use of the device according to the invention is not limited to the treatment of body fluids, but can be used for the treatment of any fluids to be examined.

The receptacle, the filter device and the cultivation device can be viewed as modules of the device, which can each be coupled with one another. Depending on the embodiment of the device described here, the filter device can be realized either as a separate component-type device in the manner of a separate filter chamber (optionally with a collection container coupled thereto) or as a module, which is integrated into the receptacle. The cultivation device can be designed to receive the filter element from the filter device. The filter device and the cultivation device can be coupled together in such a way that the filter element when transferring from the filter device into the cultivation device does not come into contact with the environment, in other words, without coming into contact with the atmosphere surrounding the device.

In this regard, the term filter element can mean in particular the surface or side of the filter element on which the (concentrated) pathogenic particles are located after the filtration. One of the objectives of the present invention is the prevention of contamination of this surface. In the case of the surface lying opposite said surface, a contact with the surrounding atmosphere is not a critical issue. The receptacle can be a suitable container for receiving the fluid, which can be formed for example from glass or a plastic and can have a cylindrical form. In the case of a filter device in the form of a separate filter chamber, said filter device can be coupled with the receptacle in a fluid-mechanical coupling, for example by means of a hose, so that the fluid located in the receptacle can be transferred into the filter device. The receptacle and the filter device can however also be plugged together, with both then having corresponding matching connections. For this purpose a Luer Lock connection system—with or without a screw thread—can be used for example.

According to further exemplary embodiments of the device, the receptacle can be a syringe and the filter device can be designed such that the fluid can be introduced from the syringe into the filter device.

According to further exemplary embodiments of the device, the filter device can be formed in the receptacle. Using embodiments of this kind it is possible to provide a particularly compact form of the device, as the filter function by means of the filter device is integrated directly into the receptacle. Devices of this kind then do not require any separate filter chamber. In order to couple the filter device to the cultivation device, the receptacle can be coupled to the cultivation device.

According to further exemplary embodiments of the device, the fluid can be blood. The device disclosed here nevertheless allows the processing of in particular body fluids such as for example urine, liquor (brain fluid) or any kind of fluid obtained by means of puncture. In a general manner, the device disclosed here can be used for any fluids in which the presence of pathogenic particles needs to be rapidly established.

According to further exemplary embodiments of the device, the receptacle can comprise a first agent, which prevents the coagulation of the blood, a so-called anticoagulant agent, and at least one second agent, which brings about a blood lysis. The second agent can for example be saponin, which in a known manner leads to the lysis of erythrocytes and leucocytes. Furthermore, other substances which are useful for treating the respective fluid can be present in the receptacle.

According to further exemplary embodiments, the device can furthermore comprise a collection container, which is coupled via a coupling point to the filter device and serves to collect the filtered fluid. The collection container can thus be provided to collect the filtered—i.e. freed of pathogenic particles—fluid. The collection container can be detachably connected to the filter device, so that upon completion of the filtering operation the collection container can be detached and the fluid collected therein can be disposed of. In exemplary embodiments, in which the receptacle and the filter device are formed in a device, for example a container, the collection container can also be formed by a part of the receptacle. For example, the filter element can then divide the receptacle into two compartments, with one compartment having the filtered fluid and the other compartment having the still unfiltered fluid enriched with pathogenic particles or towards the end of the filtering operation essentially having only the pathogenic particles from the fluid.

According to further exemplary embodiments of the device, the filter element can be rotatably mounted inside the filter device. In a general manner, the filter element can be arranged in a static or mobile manner in the filter device. The fluid can be passed through the filter element in a passive manner, i.e. for example by the force of gravity, or in an active manner, for example by pressure build-up. The filter element can be rotatably arranged in the filter device, for example at the coupling point between the filter device and the collection container, in order to rotate the surface of the filter element, on which potential microorganisms filtered out of the fluid are present, and to thus align the membrane surface of the filter element for the introduction into the cultivation device relative to said cultivation device. For this purpose operating elements can be arranged on the outside of the receptacle, by means of which the filter element can be rotated on the inside of the filter device. In one exemplary embodiment, the filter element can be a disc which fills the cross section of an essentially cylindrical filter device, on which the fluid strikes from the top from the receptacle coupled to the filter device. Following the passage of the fluid through the filter disk said filter disk can be rotated inside the filter device by 180° in order to finally be transferred through the base of the filter device into the cultivation device.

According to further exemplary embodiments, the device can have operating elements on its outside, by means of which the filter element in the filter device can be detached from its position. The operating elements can be the same operating elements by means of which the orientation of the filter element inside the filter device can be controlled. The operating elements can for example be pins, which have on one end a formed structure or a gear ring structure, which engage with a corresponding formed structure or gear ring structure, which is arranged inside two diametrically opposite openings in the filter element. In this way, torsional forces can be transferred from the outside through a wall to the filter element The operating elements can be drawn axially out of the openings, as a result of which the filter disk loses its hold on the inner wall of the filter device or of the receptacle and thus can be detached therefrom.

According to further exemplary embodiments of the device, in the interior of the receptacle a piston, which is mobile therein thanks to a piston rod that projects outwards, can be provided, which piston has a plug, which has full contact with the side walls of the receptacle. The piston can be moved by means of the piston rod and can be used to move the fluid inside the receptacle or to build up an excess pressure or a vacuum, in order to convey the fluid into or out of the receptacle. In the former case, the piston can be used to drive the fluid out of a compartment of the receptacle into another compartment of the receptacle, with the plug of the piston then being formed penetrable by the fluid in only one direction and being able to be considered as a partition wall between the compartments. The piston rod can be connected by means of a screw thread or a plug-in connection to the plug, with the unit comprised of the piston rod and plug being seen as a piston. The piston rod can be fixed on the plug even before usage of the device or can just be attached to the plug by the user after introduction of the blood (for example by means of a screw thread).

According to further exemplary embodiments of the device, the piston can comprise the filter element. For example, the filter element can be arranged on the face side of the plug of the piston, with the plug being formed penetrable by the fluid in one direction. The face side of the plug means the side which faces the interior of the receptacle and which is arranged on the side of the plug opposite the piston rod. By means of movement of the piston and thus of the filter element, said filter element can be passed through the fluid and can thus generate the desired filtering effect. The plug of the piston can however also be formed impenetrable so that, by means of its movement, the fluid can be pressed through the filter element which is separated by the plug. The piston can of course also be moved automatically, for example by means of an actuator.

According to further exemplary embodiments of the device, the piston can comprise a nutrient element. The nutrient element can be an element enriched with a physiological nutrient medium, which is arranged between the filter element and the piston rod. Alternatively, the nutrient element can also be in the form of a "dry element" and can receive the physiological fluid nutrient medium only during the filtering operation. The nutrient element can for example have the form of a thin disk and be arranged on the face side of the plug. If a cylindrical vessel is assumed to be the receptacle, the nutrient element can thus be arranged between the face side of the plug and the back side of the filter element. The nutrient element can serve to receive a fluid nutrient medium, which is located for example in the receptacle, during the filtering operation in order to serve in the subsequent analysis process as a solid nutrient medium for microorganisms which remained on the surface of the filter element and which are incubated. The solid nutrient medium and the filter element can be detachable from the plug in order to be introduced into the cultivation device. In the cultivation operation, the nutrients of the nutrient element can diffuse through the membrane of the filter element to its other side, where they are available to the microorganisms to be incubated.

The physiological nutrient medium can be (1) a non-selective minimal medium or full medium or (2) a selective or elective or differential nutrient medium. In the former case, the nutrient medium can thus be selected such that it can be used by a maximum amount of microorganisms as a metabolic basis and thus permits or facilitates the growth and increase thereof. In case two, the nutrient medium can be selected such that it supports the growth of microorganisms of only a certain type or of a group of microorganisms characterized by specific properties (e.g. resistance to antimicrobial substances or association with a group of related microorganisms) or suppresses the growth of defined microorganisms (e.g. accompanying flora which interfere with diagnosis) or already permits a preliminary characterization of microorganisms (e.g. indication of resistance); i.e. is targeted so to speak at an exclusive (selective) cultivation by only one kind or one group of microorganisms. In the latter case, the device can thus be used as a specific quick test to detect a certain kind or a defined group of pathogens.

According to further exemplary embodiments of the device, the piston can comprise an element (hereafter referred to as a flow limiter) which limits the flow of fluid, which is arranged between the filter element and the piston rod and which is designed such that its flow direction is directed against the direction of movement of the piston rod. In other words, the flow limiter is designed to permit a flow in only one direction. The flow limiter can form a part of the plug of the piston and be arranged in front of the nutrient element, i.e. on the side of the nutrient element which is opposite the filter element. The flow limiter can have a screw thread or a plug-in thread for coupling the piston rod. The flow direction of the flow limiter can be designed such that, irrespective of whether the piston is pushed through the fluid present in the receptacle from the top downwards or from the bottom upwards, the flow limiter permits passage of the fluid to be filtered, but prevents a backflow of the filtered fluid to the still unfiltered fluid. The flow limiter can be a component of a mobile partition wall, which divides the receptacle into two compartments (subareas). The flow limiter is accordingly designed such that it prevents a backflow of the filtered fluid from the compartment of the receptacle in which said fluid is accumulated into the compartment in which still unfiltered fluid is located and in a manner independent of the orientation of the device or of the receptacle. The flow limiter can be designed for example as a valve disk, and in a general manner, its cross section can be adapted to the cross section of the interior of the receptacle. The valves can be designed such that they can be opened in only one direction by means of the pressure of the fluid. With respect to its function, the flow limiter can also be referred to as a backflow limiter.

According to further exemplary embodiments of the device, the receptacle can have at least one holding element, which is arranged at the end of the receptacle which is opposite the end from which the piston rod projects. The piston can be locked by means of the at least one holding element to this end of the receptacle in such a way that at least the filter element and the element enriched with a physiological nutrient medium can be detached from the piston. The at least one holding element can be a projection, which fits into a corresponding opening in the plug of the piston and can engage therein. The at least one holding element can be designed as a hook.

According to further exemplary embodiments of the device, said device can have a cover, which is removable, with the piston being moved through an interior of the device to the cover in order to filter the pathogenic particles out of the fluid. The cover can for example be arranged on the base or on the top of the receptacle. The cover together with the plug of the piston or with the filter element together with the nutrient element, if no piston is used, can define a compartment inside the receptacle. The cover can for example form the base of the receptacle and permit access to the filter element, once it has been passed through the fluid located in the receptacle. The cover can then be removed after the filtering operation so that the filter element (together with the nutrient element, if present) can be transferred into the cultivation device.

According to further exemplary embodiments of the device, an opening can be provided in the cover, through which a vessel is coupled in a fluid-mechanical manner to the interior of the device, with the vessel for collecting a fluid enriched with solids serving for the filtering operation. The vessel can be connected to the compartment of the receptacle, in which the still unfiltered fluid is located. During the filtering operation, the amount of solid-free fluid in this compartment decreases, whereas the amount of solids remains the same due to the filtering effect of the filter element. Accordingly, the still unfiltered fluid is rich in solids. The vessel thus serves to collect a sample from this fluid rich in solids. The thus collected sample can then be tested with analysis processes other than incubation. Solids can be understood to mean here both microorganisms and blood components which differ depending on the actual application and depending on the selected filter size.

In further exemplary embodiments, a corresponding method for treating fluids, particularly body fluids, is provided. The method comprises, in the first step, receiving a fluid in a receptacle. In a subsequent step, the method comprises filtering of the fluid by means of a filter device, which has a filter element for filtering pathogenic particles out of the fluid. In a further step, the method comprises the transfer of the filter element into a cultivation device, which is designed to incubate the filtered out pathogenic particles on a nutrient medium, with the pathogenic particles being transferred from the filter element in a contamination-free manner to the cultivation device. The contamination-free transfer of the pathogenic particles from the filter element to the cultivation device refers to a transfer in which the risk of contamination with germs or other foreign substances from the environment can be reduced or entirely (to the extent possible) prevented in that, during transfer of the pathogenic particles from the filter element to the cultivation device, the filter surface on which the pathogenic particles are disposed does not come into contact with the ambient air. This can be achieved in that the device is constructed in a modular manner and the individual units can be plugged into or onto one another or can be coupled with one another in such a way that the filter element can be transferred between the units (e.g. between the receptacle and the cultivation device) through a space which is closed relative to the outside.

Furthermore, in various exemplary embodiments, an additional device for treating fluids is provided, comprising: a receptacle for receiving the fluid; a filter element, which is displaceably mounted inside the receptacle and which divides the receptacle into a first compartment and a second compartment; a flow limiter, which is displaceably mounted inside the receptacle and which is designed to permit a flow of the fluid between the compartments in only one direction; with the device being designed such that, by means of displacement of the filter element inside the receptacle, a retentate is provided in the first compartment and a filtrate is provided in the second compartment. The filtrate is the filtered fluid which can be disposed of. The retentate is the useful substance, on the basis of which potential detection of pathogenic particles in the fluid is realized.

According to one exemplary embodiment of the additional device, the flow limiter and the filter element can lie in a full and tight manner against the inner wall of the receptacle. As a result, in each step of the filtration method both the first compartment and the second compartment are tightly sealed, i.e. a contamination of the environment with substances from the compartments or vice versa cannot take place. The tightness can be realized in a similar manner to syringes in which a plug seals the interior of a syringe towards the outside.

According to one exemplary embodiment of the additional device, first holding means can be provided on the inner wall of the receptacle, so that, at the end of the treatment operation, the flow limiter can be locked by means of the first holding means inside the receptacle. The locking can occur for example by means of suitable engagement means (e.g. by means of a corresponding tongue/groove pair).

According to one exemplary embodiment, the additional device can have a removable base cover, with second holding means being provided on the inner wall of the removable base cover, so that the filer element can be locked at the end of the treatment operation by means of the second holding means in the removable base cover. The holding means can for example engage in the filter element or in a nutrient element additionally provided behind the filter element or in a framework structure, which brings together the nutrient element and the filter element in one structure.

According to one exemplary embodiment of the additional device, the flow limiter can be attached at the end of a piston rod and can be displaceable by means of the piston rod inside the receptacle. In this regard, the other device can be modeled in the first approximation on a syringe.

According to one exemplary embodiment of the additional device, the filter element can be connected at the side facing away from the piston rod of the flow limiter to said flow limiter.

According to one exemplary embodiment of the additional device, in the case of the locking of the flow limiter by means of the first holding means inside the receptacle at the end of the treatment operation, the filtrate can be enclosed in the second compartment in a contamination-free manner. A contamination-free enclosure means an enclosure in which the filtrate cannot come into contact with the environment of the second compartment. In this way, there is no contamination either of the filtrate with environmental microorganisms, or of a user or the environment with the filtrate.

According to one exemplary embodiment of the additional device, detachable points can be provided between the filter element and the flow limiter so that, when the removable base cover is removed, in which removable base cover the filter element is locked at the end of the treatment operation, the filter element remains in the removable cover and seals the retentate in the cover in a contamination-free manner. The detachable points can be for example predetermined breaking points or a screw connection.

Further advantages and features of the device according to the invention shall emerge from the exemplary embodiments described below with reference to the attached drawings.

The terms used in the following description to identify relative positions such as "top" and "bottom" refer to the location of the identified elements in the figures and are furthermore not to be understood as restrictions.

Figure 5A:
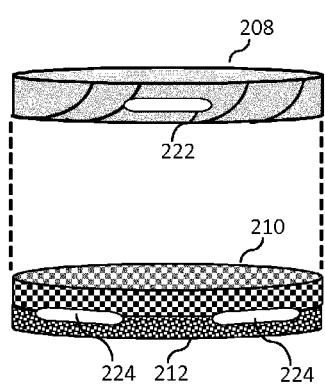

FIG. 5A separately depicts the flow limiter in a perspective top view of the nutrient element and the filter element.

Figure 5B:
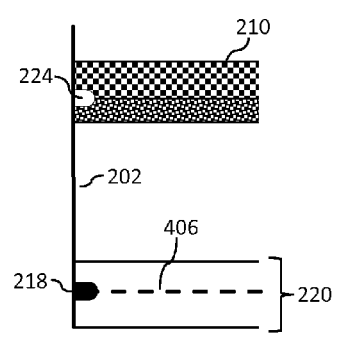

FIG. 5B shows a cross section view of a part of the unit made up of the nutrient element and the filter element depicted in FIG. 5A.

Figure 6A:
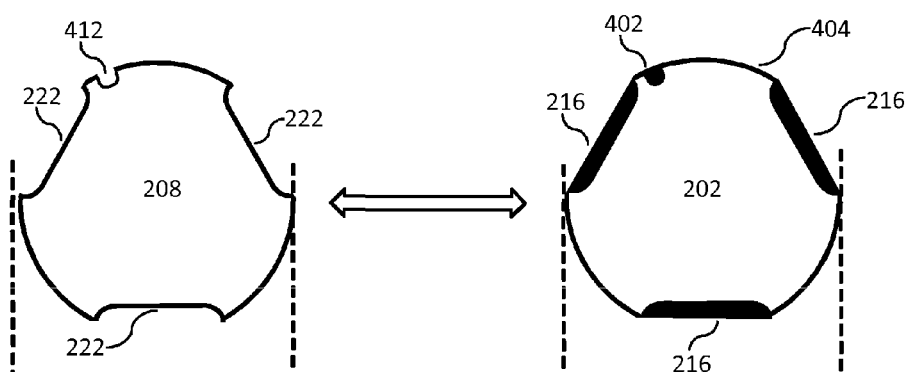

FIG. 6A depicts the cross section of the flow limiter (left) and the cross section of the receptacle of the device for treating body fluids (right), in a top view in each case.

Figure 6B:
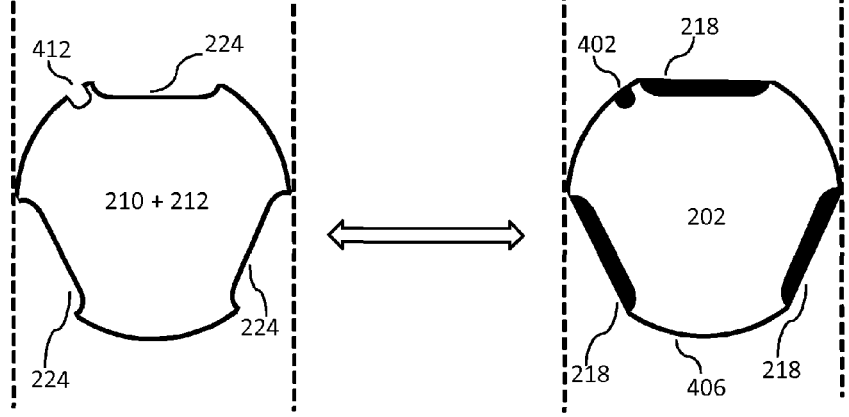

FIG. 6B depicts the cross section of the nutrient element together with a filter element (left) and the cross section of the receptacle of the device for treating body fluids (right), in a top view in each case.

Figure 1:
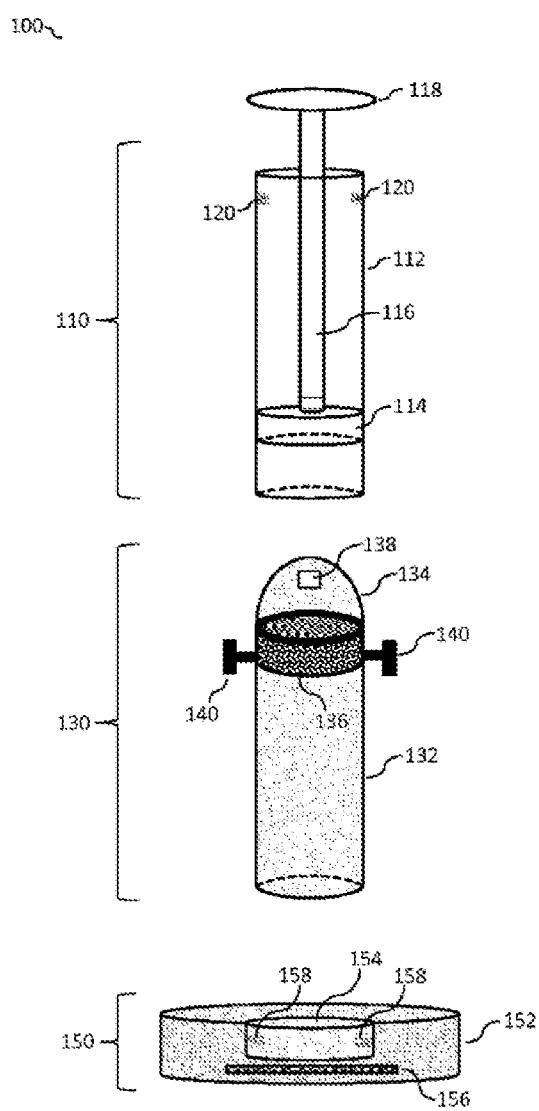
FIG. 1 shows an exemplary device for treating body fluids, in which the receptacle and the filter device are formed as individual modules.

FIG. 1 depicts a device 100 for treating body fluids according to various exemplary embodiments. The device comprises a receptacle 110, a filter device 130 and a cultivation device 150. In this exemplary embodiment, the receptacle 110 has a cylindrical container 112. The open end of the container 112 which is at the top in the figure can be sealed with a cover. The cover can also be dispensed with and the top end of the container 112 can instead remain open. The interior of the container 112 can then be hermetically sealed from the top side of the container 112 by means of a plug 114 lying inside the container 112, which serves for fluid displacement inside the container 112. A piston rod 116 is attached to the plug 114, with the mechanical connection between the piston rod 116 and the plug 114 being able to be detachable and being able to have a screw connection or a plug-in connection (not explicitly depicted in FIG. 1). In FIG. 1, a plate 118 is provided at the operating end of the piston rod 116, which plate facilitates the pressing in of the piston into and the withdrawing of the piston from the container 112. According to further exemplary embodiments of the device 100, the receptacle can be designed as a syringe, so that the plate 118 then corresponds to the thumb part and, as is standard with syringes, a finger edge can be additionally provided at the top edge of the container 112. The plug 114 can be produced from a plastic and can be displaceable in the container 112 by means of the piston rod 116. On the bottom end of the container 112 an opening is provided (not explicitly depicted in FIG. 1) by means of which a body fluid can be introduced into the receptacle 110 and also removed therefrom. In the top region of the receptacle 110 at least one fixing element 120 can be arranged, by means of which the plug can be fixed in a top position. It is thus possible for example for the piston to be fixed in the top position by means of the fixing elements 120 after the body fluid is received. The at least one fixing element 120 can have a projection or structures, which the plug 114 has the matching connection element for, so as to provide for example an engagement function. When required, the plug 114 can then be disengaged again from the fixing position. The fixing function can be based on the engagement of the fixing elements 120 in corresponding structures in the plug 114, and a rotational movement may be additionally required to activate and release the fixing functionality.

The filter device 130 depicted in this exemplary embodiment as a separate module is designed as a pieced together (e.g. plugged together) unit made up of a filter chamber 134 and a collection container 132. It has an inlet 138, by means of which it can be connected to the collection container 110 for transfer of the body fluid out of the receptacle 110 into the filter chamber 134. The filter chamber 134 has a filter element 136, which is in the form of a filter disk here. The filter element 136 to all intents and purposes divides the filter device 130 into two compartments—the filter chamber 134, into which the non-filtered body fluid can be transferred from the receptacle 110, and the collection container 132, which is arranged here beneath (with top and bottom here being able to be considered from the perspective of the action of gravity) the filter element 136. The collection container 132 is connected via an interface, for example a screw connection or plug-in connection, to the filter chamber 134 arranged above. In this exemplary embodiment the filter chamber 134 is formed in a coupled manner, so that the disk-shaped filter element 136 can be rotated inside the filter chamber 134. The rotation of the filter element 136 can be brought about by means of at least one operating element 140, for example at least one operating pin. The suspension of the filter element 136 inside the filter device 130 is detachable, so that the filter element 136 can be detached from said filter device. For this purpose, the operating elements 140 can for example be drawn radially outwards, so that they are no longer in contact with the filter element 136. Once the filtration is completed, the collection container 132 can be detached from the filter chamber 134 (or vice versa) at the interface and disposed of with the filtered fluid.

The filter chamber 134 is formed in the manner of a coupling in the depicted exemplary embodiment in order to permit a rotation of the filter element 136. The filter element

136 can be rotated 180°, so as to then "stamp" the filtered out pathogenic particles from the surface of the filter element 136 onto a cultivation device 150 which is described in more detail below. In alternative exemplary embodiments, the filter element 136 can however also differ from the flat disk shape and be formed for example in a cone shape, so that the pathogenic particles are accumulated in such a cone once the filtration has been realized.

The device 100 for treating a body fluid additionally has the cultivation device 150. The cultivation device 150 is in principle a heat-emitting device for the filter element 136, to bring about rapid incubation. The cultivation device 150 can be a dish 154 surrounded by a material 152 which conducts heat well, for example a "Petri dish" (a dish with a solid nutrient medium for the cultivation of microorganisms), with the dish 154 being removable from the material 152 surrounding it. At its outer surface not in contact with the dish 154, the material 152 having good heat-conducting qualities can have an insulating material (not explicitly depicted in FIG. 1), in order to minimize the heat loss of the cultivation device 150. The cultivation device 150 additionally has a heat-giving or heat-producing element 156 (subsequently referred to as a heating element), which can generate/give off heat on an electric, chemical or electrochemical basis, for example a heating coil or a latent heat storage element. The heating element 156 can be permanently integrated into the material 152 having good thermal conduction or can be a module, which can be inserted/plugged into said material when required. The cultivation device 150 can additionally have at least one holding element 158, which serves to fix the filter element 136 in the dish 154. The holding element 158, two of which are schematically depicted in an exemplary manner in FIG. 1, can be an element which, by means of an engagement function, fixes the filter element 136 in the dish 154, once it has been detached from the filter device 130 or from the filter chamber 134. The at least one holding element 158 can be formed on the inner surface of the dish 154, for example in the form of a curvature or a projection. The at least one holding element 158 can however also be an element which can be placed in the material 152 having good thermal conduction or on the dish 154 in order to prevent the filter element 136 falling out of the dish 154. Alternatively, the holding function, which is symbolized by the two holding elements 158 in FIG. 1, can also be realized by means of a retaining clamp or a cover, which can be placed or screwed onto the cultivation device 150 from the top.

Figure 2:
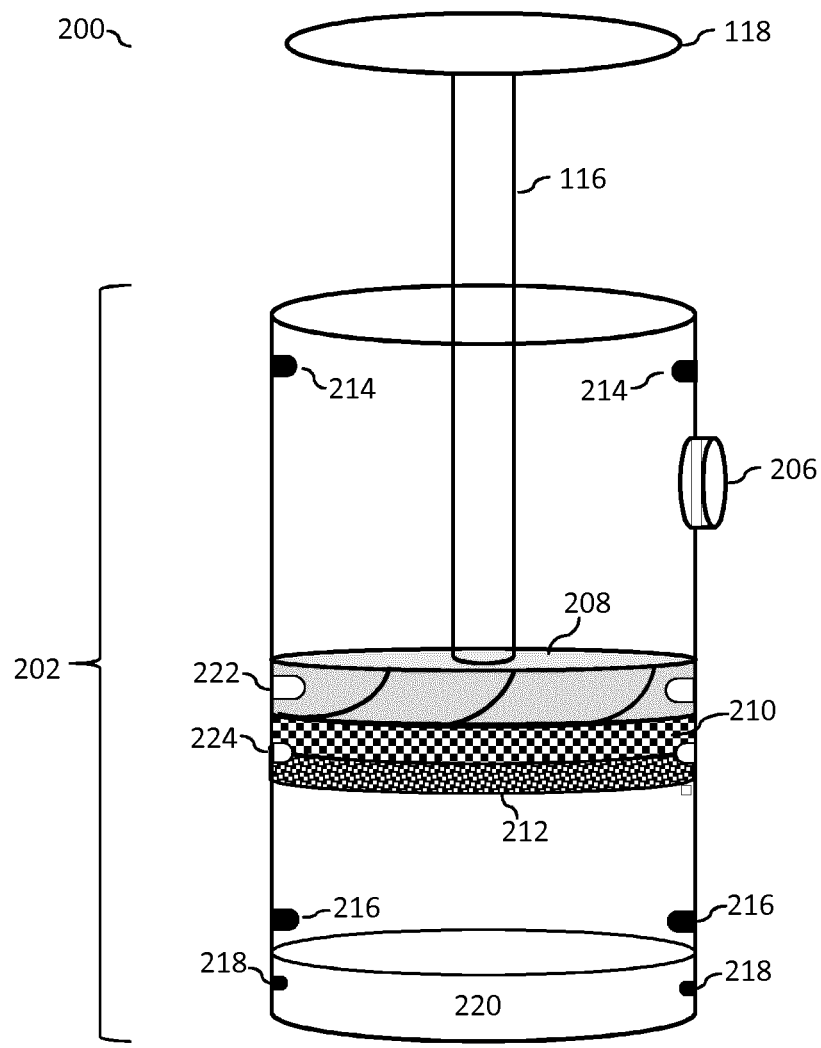
FIG. 2 shows an exemplary device for treating body fluids, in which the filter device is integrated into the receptacle.

An alternative embodiment of the device 200 for treating body fluids is depicted in FIG. 2. In the case of this device 200, as a variant of the device 100 depicted in FIG. 1, the filter device is integrated into the receptacle 202. In other words, the receptacle 202 simultaneously realizes the function of the filter chamber 134 and of the collection container 132 depicted in FIG. 1, so that the device 200 can be constructed in a more compact manner. The receptacle 202 can advantageously be formed cylindrical. The top end of the receptacle 202 can remain open or be closed with a cover. The interior is closed towards the outside at the top end of the receptacle 202 by means of a plug, which is mobile inside the receptacle 202. As in the device depicted in FIG. 1, a piston rod 116 can be attached to the plug, which piston rod can have a plate 118 on the user end for simpler operation. In this embodiment the plug has three functionally different units, which are provided with the reference numerals 208, 210 and 212.

The first unit can be the flow limiter 208. The flow limiter 208 is designed such that (when used) it permits the flow of the body fluid situated in the receptacle 202 in one direction and prevents the backflow thereof. The flow limiter 208 is designed here as a cylindrical valve disk, with the valves provided therein (not explicitly depicted in FIG. 2) being configured such that they open only in one direction, e.g. upwards as a result of a pressure applied to them from the body fluid when the piston is depressed. By contrast, when the valves are pressurized from above they remain closed and allow no fluid exchange. This functionality can be ensured for example by arranging a hinge for opening a valve on the top side of the valve disk and furthermore the opening lying behind the valve disk having a smaller cross section than the associated valve disk 208, so that the valve disk contacts on an edge when pressurized from above and thus cannot be opened downwards. The above-mentioned valve disk 208 merely constitutes an exemplary means which ensures the desired functionality—the prevention of the backflow of the body fluid from one compartment of the receptacle 202 into the other compartment of the receptacle 202. As a second unit, the nutrient element 210 can be located upstream of the flow limiter 208. Finally, as a third element, the filter element 212 can be located upstream of the nutrient element 210.

The sequence of the elements, which form the plug of the piston, can depend on which side of the receptacle 202 the body fluid is located and whether, at the start, the body fluid is under the plug and the piston is moved by pressure on the piston rod 116 from the top downwards by means of said piston rod (configuration as in FIG. 2) or whether, at the start, the body fluid lies above the plug and said plug is moved by means of pulling the piston rod 116 from the bottom upwards by means of said piston rod. In the latter case, the order of the elements 208, 210, 212 which are depicted in FIG. 2 and which form the plug can be reversed. In a general manner however, the flow limiter 208 can, in the case of suitable design, i.e. when there is no blockage of the flow elements (e.g. valves) by contacting elements, also be arranged independent of the envisaged functionality (i.e. pushing or pulling of the piston) right at the bottom or right at the top in the arrangement of the elements forming the plug. In order to later permit a good diffusion of the nutrients from the nutrient element 210 to the filter element 212, the filter element 212 will advantageously have a common boundary surface with the nutrient element 210. In a general manner, the plug divides the receptacle 208 into two compartments. In the case of the device 200 in FIG. 2, the one compartment lies inside the receptacle 202 above the flow limiter 208, whereas the other compartment is located below the flow limiter 208.

The receptacle 202 depicted in FIG. 2 additionally has an inlet 206, through which the body fluid can be introduced. The inlet 206 can be arranged, as depicted in the figure, on the side of the receptacle 202 or, if present, on its top cap (i.e. surface of the receptacle 202 under the plate 118). The inlet 206 can be sealed with a membrane in order to keep the inside of the receptacle 202 sterile. For this purpose, the inlet 206 can for example be formed as a rubber plug. For the introduction of the body fluid into the receptacle 202 the membrane or the rubber plug can be pierced with a needle. A top holding element 214 can be arranged in the top region of the receptacle 202. The top holding element 214 can be used to lock the plug in a top position as already described for the device 100 depicted in FIG. 1. For this purpose at least one corresponding counterpart element 222 can be provided for example in the flow limiter 208, so that the plug can be detachably held in the top position. The top holding element 214 can however also be a holding edge (full circumference or at least one segment), which prevents the piston from being pulled out of the receptacle 202. The holding function can also be provided by the plug itself by means of the pressure of at least one of the elements 208, 210, 212 forming it against the inner wall of the receptacle 202. In addition, a bottom holding element 216 can be arranged in the bottom region of the receptacle 202. The bottom holding element 216 can be designed to lock the plug in a bottom position inside the receptacle 202 once the filtration operation has been realized. For this purpose, elements can be arranged for example on the inner wall of the receptacle 202 in a full circumference manner or only in segments, which elements provide an engagement function with matching counterpart elements 222 arranged on the outer edge of the flow limiter 208 (e.g. pairs of matching engaging detents/engaging projections and engagement recesses). In some exemplary embodiments the structures which form the top holding element 214 can be identical to those which form the bottom holding element 216, so that for the locking or for the engagement the counterpart elements 222 can be used in both cases. In such an engaged position the nutrient element 210 together with the filter element 212 can then be detached from the flow limiter 208 in order to transfer it into the cultivation device. To permit this step, the base of the receptacle 202 is removable and can be formed for example in the form of a pluggable or screwable cover 220. Once for example the body fluid has been introduced into the receptacle 202 and the plug, in particular the filter element 212, has been pressed through the body fluid by means of pressure on the piston, the plug can engage in the bottom position and be held there by means of the bottom holding element 216. In this case, the filtrate (i.e. the filtered body fluid) is located in the first compartment lying above the plug, whereas the pathogenic particles filtered out of the body fluid are in the second compartment lying below the plug. Because the flow limiter 208 prevents the backflow of the filtered body fluid from the first compartment back to the second compartment, the cover 220 can be easily removed and the nutrient element 210 together with the filter element 212 can be manually separated from the flow limiter 208. For this purpose the nutrient element can be connected by means of a detachable connection to the flow limiter 208, for example a standard plug-in connection or rotational plug-in connection. Alternatively, predetermined breaking points can be provided between the flow limiter 208 and the filter element. The filtrate sealed in the first compartment can be reliably disposed of at the end of the filtration operation. Although the cultivation device from FIG. 1 is not explicitly depicted in FIG. 2, it is also usable in the same manner as the device for the treatment of body fluids depicted in FIG. 2.

In addition to the bottom element 216 on the inner wall of the receptacle 202, the removable cover 220 can have on its inner wall at least one additional holding element 218, the form of which is similar to that of the bottom holding element 216. The inner wall of the receptacle 202 can transition in a flush and continuous manner into the inner wall of the removable cover 220, so that the removable cover 220 comprises the bottom part of the receptacle 202 and is thus pieced together (e.g. screwed or plugged together) with the receptacle 202. In a manner similar to the at least one bottom holding element 216, the at least one additional holding element 218 can allow only engagement, but not disengagement. The additional holding element 218 can thus also be formed as a partial (for example consisting of several segments) or a full projection/bar. An additional matching counterpart element 224 can be formed in the nutrient element 210, in the filter element 212 or between same and for example be designed as a matching formed recess, which is formed fully or partially in the edge of the flow limiter 208 of the plug. As depicted in FIG. 2, the additional counterpart element 224 is formed between the nutrient element 210 and the filter element 212, which form a unit. As the holding element and counterpart element it is generally possible to use a matching combination of grooves/corrugations and projections/bars formed corresponding to same. In both cases the holding elements and counterpart elements can be formed in a full manner or formed as segments. In order to prevent the bottom holding element 216 from engaging with the additional counterpart element 224 and thus negatively affecting the functionality of the device, the pairs of holding element and counterpart element can each be formed matching one another exclusively. In other words, the bottom holding element 216 can be formed such that its functionality, for example the locking, is achieved only with the matching counterpart element 222, but not with the additional counterpart element 224. This can be achieved through a special form selection, dimensioning or location of the pairs of holding element and counterpart element, with the latter aspect being described in more detail below. In a general manner for example the bottom holding element 216 configured as a projection (correspondingly fully or as segments) can be formed so large that the additional counterpart element 224 designed as a recess (fully or as segments) is so small by comparison that it can slide past it without engaging, so that no locking is achieved with these two elements.

The additional counterpart element 224 matching the additional holding element 218 can be formed in the bottom part of the plug, for example in the edge of the nutrient element 210 contacting the inner wall of the receptacle 202 or in the edge of the filter element 212 contacting the inner wall of the receptacle 202 or also between the two elements 210, 212. By means of the additional holding element 218 the nutrient element 210 together with the filter element 212 can be separately locked by the flow limiter 208 for the purpose of detachment of these two elements from the flow limiter 208. For this purpose, the side wall of the removable cover 220 can be formed higher (e.g. ca. 1-1.5 cm), in order to allow the nutrient element 210 and the filter element 212 to be received therein. In the case of the fixation of the piston at the bottom end of the receptacle 202, the flow limiter 208 can then be locked/fixed by the bottom holding element 216 and the nutrient element 210 together with the filter element 212 can be locked/fixed by the additional holding element 218. The nutrient element 210 and the filter element 212 can be present in a common framework and thus form a unit (subsequently referred to as the unit). As already mentioned, the selective locking of the unit in the cover 220 at the end of the filtration operation can be facilitated by means of a different size of the bottom holding element 216 and of the additional holding element 218 and/or by means of different dimensions, e.g. depth or length, of the respective matching counterpart elements. As indicated in FIG. 2, for example the additional holding element 218 can be smaller than the bottom holding element 216, so that the additional counterpart element 224 which is associated with the additional holding element 218 and is thus also relatively smaller can slide past the larger bottom holding element 216 without obstacles. For this purpose flexible materials which permit compression/deformation can preferably be used, e.g. plastics like polyethylene, or rubber.

Figure 4:
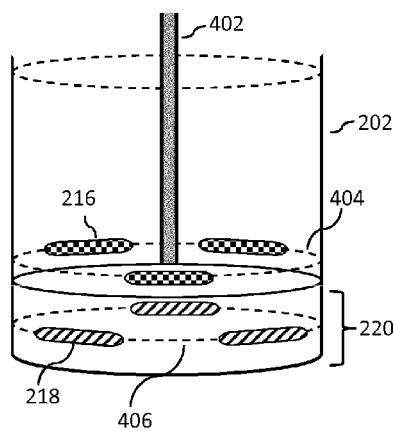
FIG. 4 shows a detailed view of the bottom region of the device for treating body fluids.

The selectivity can likewise be achieved in that the holding elements (and also accordingly the associated counterpart elements on the piston) are displaced towards one another, so that they do not lie above one another viewed in the vertical direction. To illustrate this principle, FIG. 4 depicts the bottom region of the receptacle 202 together with the cover 220 mounted thereon. To permit greater understanding, the cover 202 is depicted transparent here. As depicted, above the cover 220 on the inner wall of the receptacle 202, by way of an example three bottom holding elements 216 are depicted, which are arranged on a first circumferential line 404. On the inner wall of the cover 220 three additional holding elements 218 are depicted by way of an example, which are arranged on a second circumferential line 406. The bottom holding elements 216 are arranged offset relative to the additional holding elements 218, and are shifted in the example depicted in FIG. 4 by approximately 60°. As shown in FIG. 5A, in which in a perspective top view the flow limiter 208 is depicted separated from the unit (nutrient element 210 and filter element 212), the counterpart elements 222 are accordingly displaced by the same amount relative to the additional counterpart elements 224. When the plug is moved inside the receptacle 202, the two groups of holding element and counterpart element do not come into contact with each other, so that in this exemplary embodiment the dimensions and forms of the bottom holding elements 216 and of the additional holding elements 218 can be identical or different. FIG. 5B depicts a cross section through a part of the receptacle 202 together with the cover 220 and through a part of the unit of nutrient element 210 and filter element 212 arranged above same and depicted in FIG. 5A. According to the depicted example, the counterpart element 224 can be a blind hole and the additional holding element 218 can be a projection matching the form of the blind hole. It must however be emphasized that this form selection constitutes only one of many possibilities and other forms and dimensions also realize the envisaged function. In particular, the number of the used holding elements and counterpart elements can be selected at will and the arrangement thereof on the circumferential line must not be symmetrical.

In order to ensure that the plug does not twist inside the receptacle and thus the counterpart elements do not "align" so to speak with the associated holding elements, it is furthermore possible to provide a guide rail 402 on the inner wall of the receptacle 202. The guide rail 402 can be a structure projecting inwards from the inner wall of the receptacle 202, for example a bar, or a depression provided in the inner wall. The first solution can be advantageous, in particular in the case of thin-walled receptacles 202, which lead to compact and light devices of the type presented here. In a manner matching the guide rail 402, a structure (depression or bar) can be provided on the outer edge of the plug, which is engaged with the guide rail 402 and prevents the plug from being able to rotate about the axis of the piston rod 116 in the case of movement inside the receptacle 202.

In FIGS. 6A and 6B cross sections of layers of the plug and of the receptacle 202 are depicted, with the cross section plane extending perpendicular to the wall of the receptacle 202 and thus perpendicular to the movement axis of the piston. FIG. 6A depicts on the left the flow limiter 208 and on the right the receptacle 202 at the level of the first circumferential line 404 depicted in FIG. 4. FIG. 6B depicts on the left the nutrient element 210 together with the filter element 212 as the unit and on the right the receptacle 202 at the level of the second circumferential line 406 depicted in FIG. 4. The dashed lines are intended to indicate that the cross sections depicted in FIG. 6A are arranged precisely so over the cross sections depicted in FIG. 6B in an exemplary plug. The double arrows symbolize the association of the holding elements to the counterpart elements. In other words, in the end position of the plug, the bottom holding elements 216 are engaged with the counterpart elements 222 and the additional holding elements 218 are engaged with the additional counterpart elements 224. It can be seen in this depiction too that the arrangement of the bottom holding elements 216 is displaced relative to the arrangement of the additional holding elements 218. It is also shown that, in a manner matching the guide rail 402, which in this exemplary embodiment corresponds to a projection projecting inwards, a guide groove 412 is provided in the plug.

In a general manner, the unit can be separated from the flow limiter 208 by means of a relative movement of the removable cover 220 relative to the receptacle 202, which flow limiter is locked/fixed by means of the bottom holding element 216 in the receptacle 202, in other words for example by means of unscrewing or disconnection of the removable cover 220 from the receptacle 202. This relative movement can lead to e.g. predetermined breaking points being triggered, which can generally be for example in the form of thin plastic connection bars, which connect the flow limiter 208 to the nutrient element 210. The relative movement can also additionally or alternatively take place by means of rotation at the hand plate 118 of the piston, so that this rotation is transferred by means of the piston rod 116 to the flow limiter 208. In this case the bottom holding elements 216 can be formed such that they permit a rotation of the flow limiter 208, but not its vertical displacement inside the receptacle 202. For this purpose, the recesses in the side edge of the flow limiter 208 can be formed for example L-shaped, with the longer part of the L shape being able to extend horizontally in the side edge of the flow limiter 208, so that the flow limiter 208 can be rotated in its vertical fixed position inside the receptacle 202. The shorter part of the L shape (which extends perpendicular to the longer part of the L shape) can correspond in terms of its shape to the associated bottom holding element and can provide the engaging functionality.

In an alternative embodiment, the unit together with the flow limiter 208 can be fixed by means of the additional holding elements 218 in the removable cover 220 (e.g. by means of engagement), so that when the removable cover 220 is detached from the receptacle 202 the entire plug is separated from the piston rod 116, e.g. by means of unscrewing or disconnection of the piston rod 116 from the flow limiter 208. The flow limiter 208 can then be separated from the unit. In such an alternative embodiment, the bottom holding elements 216 (and the corresponding matching counterpart elements 222) are not required.

Irrespective of the way in which and at which stage of the overall operation the flow limiter 208 is removed from the unit, the side of the removable cover 220 on which the flow limiter 208 is exposed, is then covered with an additional cover, which from this time becomes the base of the thus formed "Petri dish", in order to be transferred in the last step into the cultivation device 150.

In another embodiment of the device 200 for treating body fluids, the inlet 206 can be formed such that it constitutes an adapter, which has a filter. This filter (second filter, prefilter) has a greater pore size (e.g. 3-12 µm) than the filter element 212 and serves for pre-filtering of the body fluid to be examined. This is advantageous for the filtering off of the larger components of the body fluid, e.g. blood clots, not lyzed blood cells, and can assist with prevention of clogging of the filter element 212 which, with respect to the prefilter, can be seen as the main filter. This functionality can alternatively also be designed such that the prefilter can be located at the bottom end of the receptacle 110 depicted in FIG. 1 (subsequently referred to as the first receptacle in this context). The agent for blood lysis and the anticoagulant means can likewise be in the first receptacle (which can also be designed in the form of a syringe and can be used for blood sampling), in which the blood lysis takes place. A first receptacle designed in this way can then be connected before the prefiltering to the inlet 206 of the receptacle 202 by means of an adapter, and during the prefiltering the filtrate— in other words, filtered body fluid without very large particles but with potentially detectable pathogenic particles— is transferred directly into the receptacle 202. This combination of a first receptacle based on a modified receptacle 110 from FIG. 1 and the receptacle 202 depicted in FIG. 2 thus provides the functionality of an additional prefiltering step and thus significantly reduces the risk of clogging of the filter element 212 of the main filter. The need for an additional syringe for blood taking is also eliminated, because this function can be provided by the first receptacle.

Figure 3:
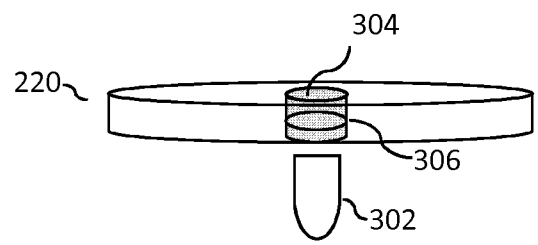
FIG. 3 shows an exemplary embodiment of a cover of the device depicted in FIG. 2.

An alternative embodiment of the removable cover 220 of the device for treating body fluid depicted in FIG. 2 is shown in FIG. 3. The cover 220 has a continuous opening 304, to which a sample vessel 302 is coupled from the outside. For this purpose, the opening 304 can have a thread 306, into which the sample vessel 302 can be screwed. Alternatively, the sample vessel 302 can also be plugged into the opening without a thread by means of a plug-in connection or can also have predetermined breaking points so that, if necessary, the sample vessel can be separated from the cover 220 in a controlled manner. At the end of the filtering process, the sample vessel 302 is filled with a body fluid, which is enriched with solids, in other words, pathogenic particles and potentially also other blood components such as for example blood cells or the proteins found in blood. In addition, the possibility of a selective enrichment with certain blood components is envisaged. This can for example be achieved through a previous selective lysis (for example only leukocytes or only erythrocytes), so that only the not lyzed fraction is enriched during filtration. Alternatively the selectivity of the enrichment can be achieved in that the filter element 212 is provided with certain specific binding molecules (e.g. antibodies) and thus the desired blood cell fractions or proteins are selectively collected on the filter. The enriched components can additionally be used for diagnostic, therapeutic or other applications. In the embodiment in which the piston is depressed for filtering, in the second compartment the quantity of solids in the body fluid drops (as it flows through the filter element 212 into the first compartment). The amount of solids in the second compartment remains the same however because they cannot pass through the filter element 212. The concentration of solids in the body fluid thus increases in the second compartment. By means of the sample vessel 302 a sample can be taken therefrom in order to be examined with other measurement methods. By means of the sample vessel 302 a body fluid volume in the range from for example 100 µl-1.5 ml with solids present in the body fluid in a concentrated form can thus be taken and evaluated in any kind of diagnostic method, e.g. by means of nucleic acid amplification technique (PCR, isothermal amplification, etc.), microarray, gene probe detection, protein detection. The compatibility of the provided opening 304 in the cover 220 with sample vessels of different volumes allows the user free selection of a certain vessel volume, which provides flexibility for different applications.

The use of the device for treating a body fluid is described below on the basis of blood as an important exemplary body fluid. However it should be emphasized here that the description below also applies to body fluids other than blood.

The blood can be taken by means of a puncture of the vessel or from an already placed catheter by means of the receptacle 110 of the device 100 according to the invention depicted in FIG. 1, which can be designed as a syringe. The sampling operation can take place in a standard manner by means of generating a vacuum by pulling on the piston, as is standard in for example the Monovette system. In a similar manner to the mentioned Monovette system, the inlet opening (not explicitly depicted in FIG. 1) on the receptacle 110 can be secured from the front by means of a protective system (adapter system), so that piercing is possible only by means of a special compatible needle, which on the one hand prevents an outflow of the blood follow collection and on the other hand prevents a contamination of the sample by environmental bacteria. Even in the receptacle 110 a fluid mixture can exist, which has a means for lysis of the blood (erythrocytes and leukocytes), e.g. saponin, and an anticoagulant means, which prevents coagulation of the blood, and potentially additional auxiliary agent. After the blood sampling, the receptacle 110 can be swished a couple of times in order to mix the blood with the lysis agent and the anticoagulant agent. Lysis of the erythrocytes and leukocytes thus occurs.

In one exemplary embodiment, the blood sampling can also take place by means of a standard syringe, e.g. Luer syringe. The blood can then be transferred with the aid of a cannula through the membrane of the inlet 206 (or the corresponding rubber plug) or with the aid of an adapter into the receptacle 202 of the device 200 depicted in FIG. 2 for the purpose of isolation of the pathogenic particles. In a further exemplary embodiment, the blood can be sampled by means of a flexible sampling catheter ("butterfly") directly in the receptacle 202. As described above, the agent for lysis of the blood and anticoagulation agent and potentially other auxiliary agents can also be present in the receptacle 202.

Irrespective of the way in which the blood is sampled, the isolation of the pathogenic particles by filtration using the filter element 208 takes place after the lysis of the blood has occurred. In a general manner, the blood can be diluted following the blood sampling and realization of lysis with diluent (e.g. 0.85% NaCl or fluid nutrient medium). The corresponding substances can be located in the receptacle before the addition of the body fluid, or can also be added to the receptacle once lysis has occurred. This makes it possible to achieve improved filterability, improved removal of the inhibiting substances and improved removal of the other blood components.

In the embodiment of the device 100 for treating body fluids depicted in FIG. 1, it is possible that, once the lysis has taken place inside the receptacle 110, the filter chamber 134 together with the collection container 132 can be connected to the receptacle 110, for example by means of a needle adapter, which is connected to the inlet 138 of the filter chamber 134. By means of pushing the piston into the receptacle 110, the fluid portion of the blood including the cellular residue which is present after lysis of the blood cells is conveyed through the filter element 136 into the collection container 132. Following the passage of the fluid portion through the filter element 136 into the collection container 132, said collection container can be separated at an interface (e.g. rotational connection or plug-in connection) from the filter element 136 and from the filter chamber 134 and disposed of. The cultivation device 150 can then be coupled at the same interface. For this purpose a matching interface can be provided in the material having good insulating properties 152 in the region of the opening provided for the dish 154. In the case of a semi-spherical design of the first compartment 134, after the connection thereof to the cultivation device, the filter element 136 can be loosened and rotated 180°. For this purpose the at least one operating element 140 can act as an external rotational wrench, by means of which the filter element 136 can be rotated inside the first compartment 134. By means of the rotation of the filter element 136, the surface of the filter element 136 on which the pathogenic particles remain in the filtering operation can be made to face the dish 154 in the cultivation device. A solid nutrient medium can be provided in the dish 154. After filtering of the blood, a small quantity of fluid (e.g. 100 μl to 2 ml) can also remain in the filter chamber 134, in which potentially present microorganisms are concentrated. This residual fluid then arrives, upon rotation of the filter element 136, at the side which faces the cultivation device 150 and can be evenly distributed in the dish 154 by means of the application of pressure on the nutrient element.

The unfiltered residual fluid which is enriched with potentially present pathogenic particles can also be taken out and examined by means of different identification methods, e.g. by means of nucleic acid amplification technique (PCR, isothermal amplification, etc.), microarray, gene probe detection, protein detection, etc. The lyzed blood can for example be driven through a cone-shaped (e.g. in the form of a 1.5 ml plastic tube) filter, with the corresponding piston (see FIG. 2) being able to be correspondingly cone-shaped at the end, so that the fluid with concentrated microorganisms is collected after full depression of the piston as a residual volume in this "plastic tube". This can be broken off (or loosened from the present screw thread) for example with incisions which are present and either placed in a leak-proof plastic tube or used in a system of any kind for further examination.

The cultivation device 150, in particular the dish 154, can have a cover, which is formed such that it provides a broad opening in the center, at which opening the syringe with the semi-spherical filter chamber is connected. The (empty) syringe remains stuck on the outside and, with the semi-spherical filter chamber with the filter, is partially pushed forwards or engaged in the opening, so that the filter comes into contact with one (or several) non-selective nutrient medium/media as a device for cultivation of the microorganisms. The microorganisms are thus transferred ("stamped") to the nutrient medium/media and can be directly cultivated (FIG. 1). The empty syringe is detached, and there is no contact with the air because the syringe was connected via an adapter to the filter chamber.

In another embodiment, after filtering of the blood through the filter element 136 and removal of the collection container 132, the filter element 136 can be loosened inside the filter chamber 134 (e.g. by means of pressing or drawing out of the operating elements 140) and directly introduced without prior rotation into the dish 154 of the cultivation device 150. The filtered out pathogenic particles can then be cultivated directly on the filter element 136 in the dish 154, with the presence of microorganisms directly resulting in the formation of colonies on the membrane of the filter element 136. Irrespective of whether the filter element 136, 212 is or is not rotated before the placement in the cultivation device 150, the side which faces away from the cultivation device 150 of the arrangement of the filter element 136, 212 and, if appropriate, the nutrient element can be sealed with a cover (if appropriate with an agar layer which the filter membrane contacts during the cultivation) and placed in the cultivation device 150. The processing takes place in a sealed and thus contamination-free manner.

In general the filter element 136, 212 can, after a realized filtration of the body fluid but before the filter is applied to the device, for the purpose of cultivation of the microorganisms, be washed for example with 0.85% NaCl or fluid nutrient medium, for example by means of introduction of such a solution into the receptacle 110, 202 and realization of a filtration operation, which is then realized with the 0.85% NaCl or the fluid nutrient medium. This makes it possible to obtain a better removal of inhibiting substances from the surface of the filter element 136, 212 and also a better removal of other blood components, which can ultimately permit better detectability of the colonies forming and better quality of the subsequent identification, e.g. by means of MALDI-TOF.

As already explained with respect to FIG. 2, the filter element 136 does not have to be located in a separate filter chamber 134, but can be fixed at the end of the piston, which is in the receptacle 110, 202. After collection of a blood sample in the receptacle 202, the fluid portion of the blood passes by means of pressure to the piston by means of the filter element 212 fixed on the end of the piston at a part of the receptacle 202, for example in the part behind the plug of the piston, while the pathogenic particles and any cellular residue present after the lysis of the blood cells remain in the corresponding other part, for example in the part in front of the plug of the piston. The potentially present pathogenic particles are "pushed forwards" and concentrated. Depending on the embodiment of the associated cultivation device 150, the pathogenic particles can then be cultivated directly on the membrane of the filter element 212 or on a nutrient medium in the cultivation device 152. The body fluid enriched with microorganisms can be removed at the end of the filtration operation and be used for other identification methods and/or sensitivity testing methods.

The embodiment depicted in FIG. 2 can have the advantage that the blood is introduced directly from the patient into the receptacle 202 (while embodiments in which blood taken previously by means of a syringe is transferred into the receptacle are not ruled out), in which lysis agents, anticoagulant agents and diluents (total volume of the fluid e.g. 100 ml) are located. The total amount of the fluid located in the receptacle can be for example 100 ml. This embodiment on the one hand permits a better filterability of the collected blood by means of the previously occurring dilution and on the other hand it does away with an additional step of transfer of the blood from a syringe into the receptacle device 202. This simplifies the processing by the medical staff at the patient's bed and allows prevention of contamination of the collected sample.

The cultivation of the microorganisms directly on the filter element 212 is facilitated in that the nutrient element 210 fixed behind the filter element 212 receives the liquid nutrient medium and acts as a "solid nutrient medium". The received nutrients can diffuse through the filter membrane to the other side of the filter membrane and can be taken up there during the incubation of growing microorganisms. The cross section form of the filter element can correspond to the internal cross section of the receptacle and can for example be formed round with an average size in the range of a few centimeters, for example 5 cm. This permits a rapid filtration without filter clogging. Furthermore, the growth of microorganisms on a large surface area permits the quantitative counting of accumulated colonies. It is also possible to arrange on the removable cover 220 of the receptacle 202 a nutrient element for cultivation of microorganisms or an agar layer can be applied in order to also permit the growth of microorganisms which remained not on the filter element 212 but on the cover 220.

Irrespective of the specific design of the receptacle and, if present, of the separate filter chamber 134, the filter element 136, 212 is incubated in the last step. The filtered out pathogenic particles are cultivated in a dish 154 on an agar or directly on the membrane of the filter element 136, 212 removed from the receptacle 202 or the filter device 130. The nutrient element 210 can either be wetted by means of the fluid nutrient medium used as a fluid for filtering or can be wetted by means of addition of a fluid nutrient medium after filtering through of the fluid portion, in order to allow the growth of the pathogens directly on the filter membrane.

The thus inoculated dish 154 is part of the cultivation device 150 or is placed in same, if it is taken out for inoculation. The cultivation device 150 is adapted to the form of the dish 154, so that the dish 154 is surrounded at least from below and from the sides. By means of heating the cultivation device to a temperature suitable for the cultivation of microorganisms, for example 35° C.-37° C. for bacteria, an incubation of the pathogens is achieved even before the arrival of the samples in the microbiological laboratory, i.e. during intermediate storage and during the sample transportation. This significantly reduces the time taken to identify pathogens. The cultivation device 150 can be designed for a dish 150 or also for several dishes simultaneously, with the number of individual cells being able to be selected as required.

With the here described device for treating fluids, which is described in numerous embodiments, a system can be realized, which in the case of the treatment of blood as a body fluid is closed in all stages from the blood sampling to the cultivation of the filtered out microorganisms. In other words, the device described here can be conceived such and its components can be coupled with one another such that all steps from the receiving of the fluid in the receptacle and the filtration to the transfer of the pathogenic particles into the cultivation device can take place in a contamination-free manner. This allows the risk of contamination to be virtually eliminated.

One form of application of the device according to the invention can be a culture-based rapid test for detection of pathogenic particles such as microorganisms in the fluid to be tested, e.g. in the blood. Such a rapid test can also be used with suspensions which have non-fluid (body) materials. For this purpose the filtration operation by means of the device according to the invention can be designed such that a certain volume of fluid remains in the receptacle, i.e. the piston is not fully depressed as far as the limit stop, but instead engages for example in a predefined intermediate position. Following the filtration the incubation then takes place. In this case the device according to the invention can be inserted or plugged into a heating device, without unscrewing the cover on the base. The filter unit is then not pushed as far as the cover and the cover is not separated—the incubation takes place in this case in the fluid phase between the filter unit and the cover. The growth takes place in the remaining fluid medium (e.g. 0.1-10 ml), in which the microorganisms or pathogenic particles are concentrated. Even if in the 10 ml residual volume specified by way of an example there is no strong concentration of the microorganisms (10 ml in blood sample volumes), the filtration operation simultaneously corresponds to a "washing step", in which the fluid phase of the fluid (e.g. of the blood) is exchanged with the fluid nutrient medium. If germs are present in the fluid (i.e. in the positive case), the growth detection can for example take place by means of a visual observation of the clouding of the residual volume. However, because in the case of blood as the fluid the clouding can be "concealed" by a reddish discoloration of the medium, growth of the pathogenic particles can be made visible by for example colorimetric visualization, for example according to a biochemical principle by means of chromogenic substances or "vitality staining", e.g. by means of addition of resazurin. By means of addition of chromogenic substances a pre-differentiation of the pathogens can take place (e.g. gram-positive or gram-negative, or belonging to a certain group of microorganisms). If the residual volume contains pathogens, the cover can be removed from the device and at least a portion of the residual volume can then be examined in another way (e.g. by means of streaking on a solid medium and cultivation of the pathogen or by means of molecular biology methods). If a cultivation is not envisaged, a physiological saline solution or a buffer (e.g. phosphate buffer) can also be used instead of a nutrient medium, by means of which greater filterability of the fluid in the receptacle can be obtained. All in all, the device according to the invention allows different fluids (with fluids originating from treatment of non-fluid ((body)) materials being included) to be subjected to a rapid sterility testing.

In all of the explicitly described and potentially conceivable exemplary embodiments of the device according to the invention, the addition of antimicrobial substances allows realization of a direct sensitivity testing of the filtered pathogens or the pathogens enriched in the residual volume. As described above, in the case of an antibiotic-resistant pathogen for example according to the biochemical principle, the growth is made visible by means of chromogenic substances or "vitality staining". Knowledge about the sensitivity/resistance of a pathogen or several pathogens to antibiotics is essential for selection of the correct treatment.

In another example of application, using the device according to the invention an examination for multiresistant pathogens or other problematic pathogens (e.g. methicillin-resistant *Staphylococcus aureus*, vancomycin-resistant enterococci, multiresistant gram-negative pathogens, etc.) can be realized. For this purpose the system according to the invention together with a swab can be used. Once the swab is brought into contact with a surface to be tested (e.g. external or internal patient surfaces or environmental surfaces), it can be introduced into the receptacle through the open end of said receptacle (i.e. not sealed by the cover) which lies opposite the piston. For this purpose the piston can be in the extended state, so that the space inside the receptacle is large enough to receive the swab. Alternatively, it is also possible for only the relevant part of the swab which has come into contact with the surface to be tested to be separated therefrom and introduced into the receptacle. The fluid nutrient medium can be already present in the receptacle or can be subsequently poured in. Finally, the receptacle can be sealed by means of the cover and the swab or at least the relevant part thereof can be shaken out in the receptacle, with the microorganisms potentially located on the swab being transferred to the fluid nutrient medium. The shaken out swab can then be removed from the receptacle by means of removal of the cover and the same or a different cover can be used to seal the receptacle again. The nutrient medium present in the receptacle with potential microorganisms from the swab contained therein can, as already described with reference to blood, be subjected to filtration by means of depression of the piston. As a result, the microorganisms potentially located in the fluid nutrient medium remain in the compartment between the piston and the removable cover. In addition, in the manner already described, the removable cover together with the filter device coupled thereto can be removed, sealed from the other side with a cap and then incubated in the cultivation device. In the case of the use of for example selective chromogenic media typical colonies are formed on the filter element. In an advantageous manner, the cap which seals the filter element towards the outside can be formed transparent or can at least have one transparent region, so that any colonies formed can be visually detected. For improved assessment of the colonies, the cover can have an integrated magnifier or an integrated magnifying region.

For a simpler handling of the device according to the invention in the additional use with the swab, the cover can have a recess from the inside, which can be arrange approximately centrally in the cover. The recess can be formed such that it can receive and fix a part of the swab so that, during the shaking out in the inside of the receptacle, it is fixed therein and can be more easily removed after the shaking out has been realized. In particular, no additional object needs to be used to take out the swab, which could potentially be contaminated, because the swab is then fixed on the bottom side of the cover which must not be grasped by the user. The optional recess can be protected by means of a seal for example of the "sealing curtain" type made of rubber or another material, in order that the top part (grip) of the swab is not contaminated during the shaking out. The sealing curtain simultaneously permits the use of any standard swab which is not permanently fixed to the cover. In such a case, the swab or its bottom part (lying opposite the grip) which is broken away at a predetermined breaking point is introduced into the device according to the invention. By means of a sealing of the device by means of a cover, the shaking out can take place "without spraying around" and contamination. Another part of the swab usually projects somewhat above the edge of a standard tube (usually to permit the removal again of the swab part). A cover with a recess and a sealing rubber curtain can then be "pierced" at this projecting part of the swab. After the shaking out, the swab is disposed of directly with the cover and another cover can be used to seal the device. Alternatively, the swab can also be firmly connected at the end of the grip side to a cover which fits on a corresponding receptacle.

The opening of the receptacle after a completed filtration operation by means of removing the cover together with the filter unit coupled thereto can also be dispensed with, so that the receptacle together with the cover is inserted into the cultivation device. It is thus possible for example in the case of use of chromogenic media for colored regions on the filter element to be viewed, which suggest a formation of colonies, through a transparent region in the cover of the receptacle and through a transparent region (e.g. transparent "window") in the cultivation device. The cultivation device together with the receptacle coupled thereto can be conveyed into the device realizing the examination. The incubation can take place immediately following removal at the removal site or during the transportation in the cultivation device. One advantage in the first case can be that only the positive samples are conveyed into the testing device, where a confirmation or further testing can be realized by means of suitable methods. The negative samples do not have to be conveyed to the testing device and can be disposed of. This allows the diagnosis process to be significantly streamlined and made more efficient in that at a very early stage of the overall process there is a concentration of the diagnostic process on samples which are positive.

For visual examination of the potentially formed colonies in the cultivation device said cultivation device can, as mentioned above, have transparent regions or can also be formed such that it has material slits, through which the surface of the filter element can be viewed. In connection with the embodiment shown in FIG. 2, the cultivation device can have an opening in the base or a transparent region therein, through which and through the transparent base cover the surface of the filter element can be viewed. This has the advantage that the entire device, as depicted in FIG. 2, can be introduced with the base cover into the cultivation device and the base cover does not have to be taken off at all. Such a procedure can further reduce the contamination risk in a dramatic manner. The base cover can be removed if one or more colonies or a microbial biomass has formed on the filter surface and these colonies are to be examined further. In other words, the process of opening the device can be limited to cases in which formation of colonies or a microbial biomass has occurred and they have to be subjected to further examination.

A filtration described in the application in a smaller vessel with simultaneous concentration of the still unfiltered fluid, for example in a sample vessel (element 302 in FIG. 3) coupled from the outside to the cover or in a disposable container, permits a variety of cultural and non-cultural diagnosis methods from the thus concentrated sample.

Based on the use of the device according to the invention together with a swab, an incomplete contamination-free sample processing can take place. This is however standard for the collection and processing of primarily non-sterile materials (such as surface swabs). In another application scenario, the manipulation and thus the probability of a contamination of the sample and the environment can be reduced. For this purpose the swab can be "shaken out" in a standard (but elastic for example) swab container with fluid medium. The swab broken away at a predetermined point remains in the swab container. Subsequently the fluid nutrient medium with any microorganisms or pathogenic particles located therein can be transferred into the receptacle. The swab container can be connected, via the inlet of the receptacle or by means of an opening in the region of the cover, to same, so that the fluid nutrient medium can be transferred into the receptacle (e.g. by means of pressing together the elastic container with the swab). During this process the piston can be located in an extended position (as in the case of a filled syringe).

The interface between the interior of the receptacle and its environment can be for example in the form of an opening covered with rubber, which can be pierced when required, or in the form of an adapter. During this process the broken off swab can remain in the swab container and ultimately be disposed of surrounded by same.

According to another exemplary embodiment, an additional opening can be formed in the side wall of the receptacle in the vicinity of the removable cover (i.e. at the bottom end of the device). This opening can for example project like the "nose" of a syringe in the form of a channel extending outwards from the side wall of the receptacle (for example perpendicular there to) or it can be formed as an adapter with for example a rubber cap. At the start of the method in the case of use of a device with such an additional opening the piston plug including the filter unit can be located at the bottom end of the device, i.e. on the removable cover. By means of dipping the additional opening into the fluid to be examined, a drawing out of the piston can generate a vacuum inside the receptacle, so that the fluid to be examined is, as in the filling of the syringe, drawn into the receptacle. Following closure of the additional opening, e.g. with a standard stopper, the movement of the piston in the opposite direction occurs, in other words from the top part of the device to the cover at the bottom end of the device. The outflow of the fluid through the additional opening is then prevented and the filtration of the fluid from one compartment of the device into the other occurs, as already described above with the preferred subsequent cultivation of the pathogen. In another embodiment, the additional opening can be formed as a closable valve or a closable tap.

A certain quantity of the nutrient medium can be contained between the removable cover and the piston plug including the filter unit before the start of the method, in order to permit the subsequent cultivation of the pathogen. The nutrient medium can also be contained in the form of the dry powder, which is dissolved when the fluid is drawn up and then constitutes a fluid nutrient medium.

This embodiment of the device according to the invention and methods based thereon are particularly suitable for sterility tests, in particular for the use in conditions in which a device which is able to realize microbiological tests is not available and there is a need to rapidly determine whether a fluid is contaminated with microorganisms. By means of addition of the specific indicators, as described above, it is possible to determine whether or not certain microorganisms are present. Because the device permits minimization of the work steps and thus minimizes the risk of contact with potentially dangerous microorganisms or fluids, this embodiment is particularly suitable for various field tests. To prevent potential contact of study personnel with potentially dangerous cultivated microorganisms, according to additional embodiments the cover can be not easily removed (e.g. welded shut or non-detachably locked). The growth can nevertheless be viewed through a transparent cover.

The invention claimed is:

1. A device for treating a fluid, comprising:
a receptacle for receiving the fluid;
a piston located in the interior of the receptacle in full circumferential contact with a side wall of the receptacle, the piston being movable within the receptacle by means of an outwardly projecting piston rod;
a filter device, which comprises a filter element that is connected to, and moves with, the piston for filtering pathogenic particles out of the fluid, and a solid nutrient providing element that is located between the filter element and the piston rod comprising a nutrient medium, that is configured to provide said nutrient medium to the filter element and the filtered pathogenic particles, and that has a common boundary surface with the filter element, wherein the nutrient providing element and the nutrient medium are located directly behind the filter element during filtering; and
a cultivation device, which is designed to incubate the filtered pathogenic particles and which comprises a heat-emitting device, wherein the filter device can be coupled with the cultivation device in such a way that the pathogenic particles can be transferred in a contamination-free manner with the filter element to the cultivation device.

2. The device according to claim 1, wherein the receptacle is and piston are part of a syringe and the filter device is designed such that the fluid can be introduced from the syringe into the filter device.

3. The device according to claim 1, wherein the filter device is formed in the receptacle.

4. The device according to claim 1, wherein the fluid is blood; and
wherein the receptacle has a first agent, which prevents the coagulation of the blood, and at least one second agent, which brings about a lysis of the blood.

5. The device according to claim 1, further comprising a collection container which serves to collect the filtered fluid.

6. The device according to claim 1, wherein the piston comprises an element that prevents a flow of the fluid in the direction of movement of the piston rod, which element is arranged between the filter element and the piston rod.

7. The device according to claim 1, wherein the receptacle has at least one holding element, which is arranged on a first end of the receptacle lying opposite a second end from which the piston rod projects, and wherein the piston can be locked by means of the at least one holding element in such a way that at least the filter element and the nutrient providing element are detachable from the piston.

8. The device according to claim 1, wherein the nutrient providing element is an element enriched with the nutrient medium.

9. The device according to claim 8, wherein the nutrient medium is one of the following: a solid nutrient medium and a dry nutrient powder.

10. The device according to claim 1, wherein the common boundary surface comprises a substantially full surface contact of the nutrient providing element with the filter element.

11. The device according to claim 1, wherein the nutrient providing element is configured to release the nutrient medium to the filter element by diffusion during cultivation.

12. The device according to claim 1, wherein the nutrient providing element is a disk.

13. The device according to claim 1, wherein the nutrient providing element is directly fixed behind the filter element.

14. The device according to claim 1, wherein the device is at least partially modular and the pathogenic particles are transferred to the cultivation device by transferring at least the filter device comprising at least the filter element and the nutrient providing element into the cultivation device.

15. The device according to claim 1, wherein at least one of the following group comprises at least one transparent region: the receptacle, the filter device, and the cultivation device.

* * * * *